United States Patent
Scott et al.

(10) Patent No.: US 11,547,325 B2
(45) Date of Patent: Jan. 10, 2023

(54) METHOD AND APPARATUS FOR ASSESSING SENSORIMOTOR PERFORMANCE

(71) Applicant: Queen's University at Kingston, Kingston (CA)

(72) Inventors: Stephen H. Scott, Kingston (CA); Kayne Park, Cambridge (CA)

(73) Assignee: Queen's University at Kingston, Kingston (CA)

( * ) Notice: Subject to any disclaimer, the term of this patent is extended or adjusted under 35 U.S.C. 154(b) by 550 days.

(21) Appl. No.: 16/408,656

(22) Filed: May 10, 2019

(65) Prior Publication Data

US 2019/0343430 A1 Nov. 14, 2019

Related U.S. Application Data

(60) Provisional application No. 62/669,714, filed on May 10, 2018.

(51) Int. Cl.
  *A61B 5/11* (2006.01)
  *A61B 5/16* (2006.01)
  *A61B 5/00* (2006.01)

(52) U.S. Cl.
  CPC ............ *A61B 5/1124* (2013.01); *A61B 5/162* (2013.01); *A61B 5/6828* (2013.01); *A61B 5/7475* (2013.01)

(58) Field of Classification Search
  CPC ....... A61B 5/1124; A61B 5/1126; A61B 5/11; A61B 5/4076; A61B 5/4064; A61B 5/162
  See application file for complete search history.

(56) References Cited

U.S. PATENT DOCUMENTS 8,740,794 B2 * 6/2014 Scott ................ A61B 5/743
                                                          600/301

OTHER PUBLICATIONS

Bourke, T.C., Coderre, A.M., Bagg, S.D., Dukeiow, S.P., Norman, K.E. and Scots, S.H. Impaired corrective responses to postural perturbations of the arm in individuals with subacute stroke. Journal of Neuroengineering and Rehabilitation 12:7 (2015).

(Continued)

*Primary Examiner* — Devin B Henson
*Assistant Examiner* — H. Q. Nguyen
(74) *Attorney, Agent, or Firm* — Stephen J. Scribner

(57) ABSTRACT

A method and apparatus for quantifying differences in human sensorimotor performance useful for diagnosing, assessing, and/or detecting brain injury and/or a neurological disorder, or identifying exceptional performance in a subject. In a task a subject's limb movement is restricted to a limited workspace and an object moves towards the limb. The objective of the task is for the subject to contact the object with the limb within a set time period. During the task a perturbation directed to the object and/or limb, or other feature of the environment, may occur on some trials, requiring a rapid motor correction in order to contact the object, or the subject may receive an alternative instruction on whether to interact with the object. Position data and/or motion data and/or kinetic data of the limb or portions thereof with respect to a presented object are obtained, and a data set is acquired for a plurality of trials. The acquired data set provides information about brain injury and/or a neurological disorder in the subject or exceptional capabilities of the subject.

17 Claims, 7 Drawing Sheets

(56) References Cited

OTHER PUBLICATIONS

Brenner, E. & Smeets, J.B.J. Fast corrections of movements with a computer mouse. Spatial Vision 16, 365-376 (2003).
Cluff, T., Scott, S.H. Apparent and actual trajectory control depend on the behavioural context in upper limb motor tasks. Journal of Neuroscience 35(36):12465-12476 (2015a).
Cluff, T., Crevecoeur, F. and Scott, S.H. A perspective on muitisensory integration and rapid perturbation responses. Vision Research 110:215-222 (2015b).
Crevecouer, F., Kurtzer, I., Bourke, T. and Scott, S.H. Feedback responses rapidly scale with the urgency to correct external perturbations. Journal of Neurophysiology 110:1323-1332 (2013).
Goodale, M.A., Pelisson, D. & Prablana, C. Large adjustments in visually guided reaching do not depend on vision of the hand or perception of target displacement. Nature 320, 748-750 (1986).
Lowrey, C. R., Bourke, T. C., Bagg, S. D., Dukeiow, S. P., & Scott, S. H. (2019). A robot-based behavioural task to quantify impairments in rapid motor decisions and actions after stroke. Journal of NeuroEngineering and Rehabilitation.
Piseila, L. Grea, H Tilikete, C., Vighetto, A., Desmurget, M., Rode. G., . . . Rossetti, Y. (2000), An 'automatic pilot' for the hand in human posterior parietal cortex: toward reinterpreting optic ataxia. Nature Neuroscience, 729-736.
Tyryshkin, K., Coderre, A. M., Glasgow, J. I., Harter, T. M., Bagg, S. D., Dukelow. S, P., & Scott, S. H. (2014). A robotic object hitting task to quantify sensorimotor impairments in participants with stroke. Journal of NeuroEngineering and Rehabilitation, 11(1):47.
Verbruggen, F., Aron, A. R. Band, G. P., Beste, C., Bissett, P. G., Brockett, A. T., . . . Paré, M. (2019). A consensus guide to capturing the ability to inhibit actions and impulsive behaviors in the stop-signal task. eLife, e46323.
Zago, M., McIntyre, J., Senot, P., & Lacquaniti, F. (2009). Visuo-motor coordination and internal models for object interception. Experimental Brain Research, 571-604.

\* cited by examiner

A: Baseline Trial

Step 1: Move white paddle into small rectangle

Step 2: Ball moves down workspace

Step 3: Subject uses paddle to hit ball

B: Sensory Events

Mechanical disturbance with vision

Mechanical disturbance without vision

Cursor Jump

Target Jump

Task Switch: Don't Hit

METHOD AND APPARATUS FOR ASSESSING SENSORIMOTOR PERFORMANCE

RELATED APPLICATION

This application claims the benefit of the filing date of Application No. 62/669,714, filed on 10 May 2018, the contents of which are incorporated herein in their entirety.

BACKGROUND

A key aspect of our ability to move and interact within the environment is the ability to rapidly respond to motor errors or changes in the environment and continue to perform a motor action. For example, a hockey player may be skating down the ice with the puck and gets bumped by an opposing player or the hockey stick of the opposing player may redirect the puck along the ice. Skilled players will quickly adjust their movements to continue to skate down the ice or quickly move the stick to regain control of the puck. In other cases, we use contextual signals to alter ongoing motor actions. For example, a green traffic light signals that you can continue moving and proceed through the intersection, but the light can quickly change to yellow signaling you must stop moving if not presently near the intersection.

Our ability to make these goal-directed motor corrections are a hallmark of our voluntary motor systems allowing us to move and interact in a complex world (Scott, 2016). This rapid processing of sensory information to guide our movements is supported by broad cortical and sub-cortical circuits. Neurological disease and injury can damage these brain circuits and impact our ability to make rapid motor corrections, impacting our ability to perform a broad range of daily activities. Critically, different types of sensory feedback involve partially separate brain circuits so that focal lesions or impairments in brain circuits may impact the use of one sensory feedback pathway and not another. For example, lesion of the dorsal column-medial lemniscus pathway or primary somatosensory cortex will impact the use of sensory information from the limb, but not impact visual feedback (Kandel et al., 2013).

Clinical assessment plays a crucial role in all facets of patient care from diagnosis to prognosis as well as managing all aspects of patient care (Van Duesen and Brunt, 1997). Many areas of medicine rely on a broad range of technologies to assess body structure and function to aid clinical assessment. However, assessment of brain function continues to rely largely on subjective assessment through visual or physical inspection of the patient by a clinician. Traditional clinical scales use relatively coarse ordinal scales to ensure reliability, but also make it difficult to measure subtle but potentially important changes in performance across time.

There are essentially no standard clinical tools to accurately assess the ability of a subject to generate rapid motor corrections. The standard test of asking a subject to repeatedly touch their nose and the clinician's finger can involve the clinician abruptly moving their hand to a new spatial location so that the subject must generate a corrective response to this new location. As well, assessment of whole-body balance control can involve the clinician supporting a patient as they lean forward and then releasing their support to observe how the subject generates a corrective response to maintain balance. However, in healthy subjects, motor commands to muscles for these goal-directed motor corrections or corrections to maintain balance occur in as little as 100 ms, leading to changes in limb motion in under 200 ms (Cluff et al. 2015a; Scott, 2016). Given a standard blink of an eye takes 200 to 300 ms, it is very difficult for anyone to observe even a 50% slowing in the speed of such corrections by visual inspection.

Automated processes have been developed such as computer-based assessments. For example, CANTAB (Cambridge Cognition Ltd., Cambridge, U.K.) provides a range of behavioural tasks to assess various aspects of cognitive function, including measurements of reaction time to press or release a button when a sensory stimuli is presented on a computer screen. However, research now highlights that reaction time tasks capture only one aspect of how sensory information may be used, in this case to switch from one motor action to another, from holding a button, to lifting the hand to stop contact with the button (Scott, 2016). Importantly, such tasks do not assess how sensory information is used to guide an ongoing motor action.

Robotic technology provides one potential approach to provide a precise, objective measure of sensory, motor, and/or cognitive functions. This technology can measure subject performance during various tasks and quantify subject performance based on comparisons to performance of healthy subjects. For example, BKIN Technologies Ltd. (Kingston, Ontario, Canada) has developed a suite of tasks that assess brain functions including limb position sense, visual-guided reaching, rapid motor actions, as well as various tasks that also engage cognitive processes. However, none of these tasks directly assesses the ability of a subject to generate rapid motor corrections.

A number of studies have used either visual or mechanical disturbances as a subject performs tasks such as reaching to a spatial goal (Goodale et al. 1986; Brenner and Smeets, 2003; Cluff et al. 2015a; for Review see Cluff et al. 2015b). Visual disturbances are commonly either a shift of the position of the goal (target jump) or shift of a cursor representing the position of the subject's hand on a computer screen (cursor jump). Mechanical disturbances can also be applied to the limb, altering its motion towards the spatial goal, and requiring the subject to generate a motor correction to attain the goal. In order to ensure a subject does not anticipate the visual or mechanical disturbances, many reaching trials do not have any disturbance, allowing measures of the performance of the subject during unperturbed reaching.

While reaching tasks provide a useful task for basic and clinical research, there are several problems with using such techniques clinically. Notable is the substantial amount of time to complete enough reaching trials to quantify reliably the performance of a subject. For example, a single reaching trial requires the subject to maintain their hand at a start position, reach to the spatial goal when it is presented, stabilize their hand briefly at the spatial goal, and then return to the start position to start the next trial. For healthy subjects, such trials take ~6 seconds to complete, then assessment of a single type of sensory feedback will take approximately 2.5 minutes (time based on two mechanical disturbances that push the hand laterally one direction or the other from the target, 12 trials of each disturbance and half of all trials do not include a disturbance). As sensory feedback involves many different pathways, one can have impairments in one type of feedback process and not another. Assessment of each of these pathways quickly increases the time necessary to assess a subject's ability to generate rapid motor corrections. For patients with difficulties making reaching movements the time to complete a single trial can quickly increase to 10 seconds or more. Thus, accurate assessment of four different types of sensory feedback processing can quickly increase to 20 minutes for various patient groups.

Another problem is that subjects with poor motor abilities may be much slower and not follow a roughly direct path to the goal (Coderre et al., 2010). These substantial differences in non-perturbed reaching make it difficult to directly compare their motor corrections relative to healthy subjects that display a stereotypical bell-shaped velocity profile and move relatively straight to the spatial goal (Morasso 1981; Sergio and Scott, 1999). Simple postural tasks have been used to quantify motor corrections to mechanical disturbances (Bourke et al., 2014). However, exploring motor corrections for target jumps (the goal) versus cursor jumps (representing the subject's hand) will be difficult to assess as the collinearity of the goal and cursor before the jump means subjects must immediately recognize whether the jump in the visual feedback is the goal or hand position. Specifically, a shift of the goal to the right requires a motor correction of the hand to the right. In contrast, a shift of the cursor to the right requires a motor correction of the hand to the left to attain the goal. This opposing response due to the collinearity of the target and hand likely impacts response time particularly for patient groups.

SUMMARY

According to one aspect of the invention there is provided a method for assessing sensorimotor performance of a subject, comprising: i) restricting movement of at least one portion of a limb of the subject to movement within a workspace; ii) presenting an object to the subject, wherein the object moves towards a position of the at least one portion of the limb in the workspace; iii) obtaining position data and/or motion data and/or kinetic data of the limb or one or more portions thereof with respect to the object as the subject interacts with the object; iv) restricting the time period during which the subject can interact with the object to a set time period; v) repeating ii, iii, and iv for a plurality of trials; wherein, for a portion of the plurality of trials, a perturbation is used; wherein the perturbation is a change related to the subject, object, or other stimuli; v) constructing a data set from the obtained position data and/or motion data and/or kinetic data for the plurality of trials; and vi) analyzing the data set and outputting a result that provides information about sensorimotor performance in the subject.

In various embodiments, each perturbation may be the same or different and is selected from perturbing the movement of the object, perturbing motion of the limb or the at least one portion thereof, and changing a feature of the object such that the subject must respond to the change by either interacting with the object or avoid interacting with the object.

In one embodiment the time period is adjusted according to a selected perturbation.

In one embodiment the time period is randomly adjusted to include both the set time period and a time period longer than the set time period.

In one embodiment at least one perturbation includes changing a feature of the object such that the subject must respond to the change by either interacting with the object or avoid interacting with the object requires that the subject's motor response is different than the motor response initially instructed.

The method may comprise using data acquisition apparatus to obtain position data and/or motion data and/or kinetic data of the limb or the at least one portion of the limb with respect to a presented object.

The method may comprise obtaining data relating to one or more autonomic functions of the subject.

The method may comprise presenting objects to the subject using virtual reality or augmented reality in two or three dimensions.

The method may comprise using a mechanical linkage to obtain position data and/or motion data and/or kinetic data of the limb or the at least one portion of the limb.

The method may comprise using a motion tracking system to obtain position data and/or motion data and/or kinetic data of the limb or the at least one portion of the limb.

The method may comprise determining kinetic trajectory data of the limb or the at least one portion of the limb with respect to a presented object.

The method may comprise determining speed and/or velocity of the limb or the at least one portion of the limb with respect to a presented object.

The method may comprise obtaining gaze position data as the subject interacts with the presented objects.

In one embodiment, obtaining position data and/or motion data and/or kinetic data of the limb or the at least one portion of the limb comprises using a mechanical linkage attached to the limb, or a mechanical linkage grasped by the subject, or one or more sensors attached to the limb, and related hardware for detecting output signals from the one or more sensors.

In one embodiment, assessing comprises diagnosing or detecting brain injury and/or a neurological disorder of the subject; wherein the result provides information about brain injury and/or a neurological disorder motor activity in the subject.

In one embodiment, assessing comprises determining skill level of the subject performing an activity; wherein the result provides information about skill level in the subject. The activity may be a sport.

According to another aspect of the invention there is provided an apparatus for assessing sensorimotor performance of a subject as described herein.

In one embodiment the apparatus for assessing sensorimotor performance of a subject comprises: mechanical linkage configured to be attached to a limb of the subject or grasped by the subject, wherein the mechanical linkage is adapted restrict movement of the limb or at least one portion of the limb to movement within a workspace; object apparatus that presents an object to the subject, wherein the object moves towards a position of the at least one portion of the limb in within the workspace; data acquisition apparatus that obtains one or more of position data, motion data, and kinetic data of the limb or the at least one portion of the limb as the subject interacts with the object during a plurality of trials within the workspace; wherein the mechanical linkage is adapted to apply a perturbation to the limb or the at least one portion of the limb as the subject interacts with the object during a portion of the plurality of trials; and/or wherein the object apparatus is adapted to apply a perturbation to the object as the subject interacts with the object during a portion of the plurality of trials.

In one embodiment the object apparatus is adapted to change at least one feature of the object. In one embodiment the object apparatus presents an object to the subject using virtual reality or augmented reality in two or three dimensions.

BRIEF DESCRIPTION OF THE DRAWINGS

In order to show more clearly the invention and how it may be carried out into effect, embodiments will now be described, by way of example, with reference to the accompanying drawings, wherein.

DETAILED DESCRIPTION OF EMBODIMENTS

Figure 1A:
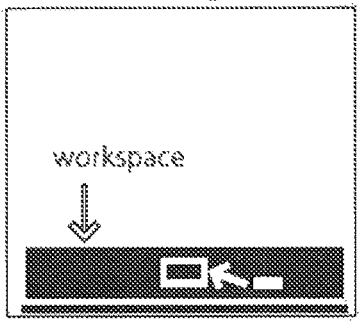
FIG. 1A is a schematic representation of a baseline trial for a fast feedback object intercept task, wherein the goal of the task is to hit a moving ball with a virtual paddle as it passes through a workspace.
Figure 1A:
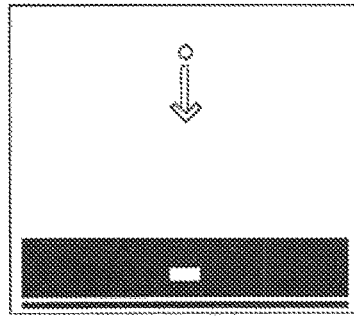
Figure 1A:
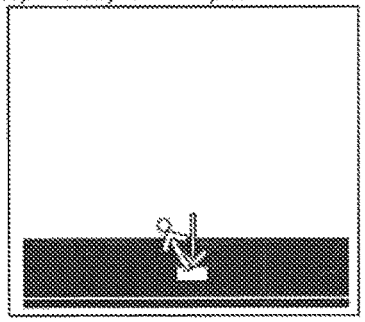

A key feature of motor function is to quickly respond to errors or disturbances when we move and interact in the world. For example, a hockey player about to shoot the puck at the net may be bumped by an opposing player. In this case, highly skilled players quickly adjust their body movement and where they shoot the puck to their advantage. This ability to rapidly respond to changes in the environment occur in many daily activities such as moving through a crowded shopping mall or when one must grab an object falling off a table. In some cases, one may try to grab the falling object or use a foot to absorb the fall if it is an apple. However, one needs to avoid the automatic response to grab the object if it is a sharp object such as a knife. Brain injuries and/or neurological disorders may impair the ability of subjects to rapidly use sensory information to select and guide our motor actions. However, such impairments cannot be assessed satisfactorily with currently-available procedures, but would be of great benefit to provide knowledge on the presence of brain injuries and neurological diseases. In cases where baseline testing is performed, such tests also need to ensure that subjects are not malingering, i.e., they are performing to the best of their abilities.

At the other end of the spectrum of human performance, elite athletes possess superior speed and agility to perform motor actions far better than most individuals. As noted above, hockey players make rapid corrections whether they are bumped by an opponent or can stop a puck moving quickly passed them. There is considerable interest to identify individuals with superior speed, strength, and skill level depending on the sport. For example, professional sports commonly have training camps (e.g. National Football League Scouting Combine, National Basketball Association Draft Combine, Major League Soccer Combine) where individuals perform physical and mental tests to assess their abilities, such as time for a 40-yard dash, bench press, or vertical jump, etc. Given the importance of rapid feedback processing to make quick corrections in sport, knowledge about the ability of individuals to generate these motor corrections related to body movement and the environment would be of great benefit for identifying individuals with exceptional skill and significant potential at sport.

There is growing concern with regards to the number of concussions in athletics and the long term impact of these injuries on an individual's health. Standard assessment tools such as Sport Concussion Assessment Tool-3$^{rd}$ edition (SCAT3) assess a broad range of brain processes based on visual/inspection of the subject and scoring of the subject's symptoms. A computer-based assessment tool is also available (ImPACT Applications, Inc.). As there is considerable subject-to-subject variability in the capabilities of individuals, a common approach is to have an athlete's pre-season baseline test and then compare performance after an event has occurred that may have given the individual a concussion. Even if the subject is within the normal range for healthy controls a drop in performance from baseline provides an indication that the subject may have had a concussion and thus evidence that the subject should be removed from the game and allowed to rest. However, since athletes usually do not want to risk being removed from the game, they can underperform during their baseline test in order to provide some 'buffer' for a post-event assessment. A major challenge is to ensure subjects are not malingering during their baseline testing to ensure an accurate comparison of performance can be made between baseline and post-event testing. A similar malingering problem can occur in the military related to whether an individual can be safely redeployed after an event has occurred during combat.

Described herein is an apparatus and a method for obtaining data on the motion, position, and/or kinetics of a limb (e.g., an arm) of a subject with respect to a real and/or virtual object in a restricted workspace, to assess sensorimotor performance of the subject. The data correspond to the subject's behavior with respect to the object, in the subject's workspace. The behavior may include reacting to and interacting with the object or doing nothing with respect to an object. In particular, the data are obtained for a subject performing a task during a limited or "set" period of time, such that in order to interact (or not interact) with an object the subject must use a fast task-dependent feedback pathway. The data are obtained by first providing time for a subject to prepare a motor action, in this case, to maintain a fixed position and wait for contact with an object moving towards the subject, and then by limiting the time between when there is a perturbation (i.e., a change in the environment related to the subject, object, or other stimuli) and when the subject can interact or not interact with the object. Examples of such times (and related distances) are provided in the below example; however, it will be appreciated other times and distances may be used. The apparatus and methods are useful for obtaining data from healthy controls, and particularly for obtaining data from subjects with injuries and/or disorders that impact brain function, as they may aid in the diagnosis, prognosis, and treatment strategies for such individuals. The apparatus and methods are also useful for obtaining data relating to a subject's ability to make rapid motor corrections with respect to particular activities such as a sport, since knowledge about the ability of an individual to generate rapid motor corrections related to body movement and the environment are of benefit for identifying individuals with exceptional skill and significant potential at the activity, sport, etc.

In the embodiments described herein, position and/or motion and/or kinetics of the limb may be monitored, and the data recorded for analysis. Position and/or motion and/or kinetics of the entire limb (e.g., for the arms: upper arm, forearm, hand, one or more fingers or thumb) or any such segment or portion thereof, individually or in combination, may be monitored and data recorded. Position and/or motion and/or kinetics of the limb joints (i.e., shoulder, elbow, wrist, etc.) may be monitored and data recorded. Segments and/or joints of the leg may also be recorded.

In one embodiment, wired or wireless sensors may be attached to the limb segments and/or joints. The sensors are used to monitor limb position and/or motion and/or kinetics in two-dimensional or three-dimensional space, as the subject interacts with the object presented to the subject.

In another embodiment, position and/or motion and/or kinetics may be monitored by one or more cameras in two- or three-dimensional space, as the subject interacts with the object presented to the subject.

In another embodiment, position and/or motion and/or kinetics may be monitored by a mechanical linkage such as that described in detail in U.S. Pat. No. 6,155,993 issued 5 Dec. 2000 to Scott, and shown in FIG. 1C. Briefly, referring to FIG. 1C, the mechanical linkage 110 is attached to the limb 100a or grasped by the subject 100. One or more sensor 115 and/or a motion tracking system 120 may track position and/or motion and/or kinetics of the limb or portion thereof. Robotic/mechanical linkages provide the ability to apply physical loads to the limb or portion thereof or simulate contact with the virtual objects 130 presented to the subject.

In the embodiments described herein objects presented to the subject may be real or virtual objects. Virtual objects may be presented using a display screen and/or projector, or virtual reality goggles or other virtual reality or augmented reality system.

As used herein, the term "virtual reality" or "VR" refers to an artificial environment into which a subject may completely or partially immerse him/herself and allow them to interact with the virtual object. The VR may be two or three-dimensional using suitable technology. For example, the artificial environment may be computer-generated allowing the subject to immerse into and/or interact with the environment.

Various embodiments may include one or more of:
the subject may be standing or sitting;
the subject may have to use both arms to interact with separate objects where contact with an object is synchronous for the two arms or asynchronous for the two arms;
the subject may have to use legs to control the paddle or other object;
the subject may have to use whole-body motion or ground reaction forces to move the paddle (or other object) to intercept moving targets;
presentation of multiple objects with one object about to hit the paddle and other objects present and moving towards different parts of the workspace, where visual and mechanical disturbances could make it an advantageous to switch to another target;
multiple events occur simultaneously, for example, both the cursor and target jump to the right and in this case no corrective response is required, or the cursor and target jump in opposite directions requiring a larger correction;
a change in speed of the objects presented;
catch trials that permit more time between the change in perturbation versus the time when the object is intercepted in order to determine whether a subject is trying their best or malingering.

Embodiments will be further described by way of the following non-limiting Example.

Example: Object Interception Task

The approach is to control the time that the subject is given to contact an object, and, prior to contact, modify information presented to the subject related to the goal or limb that requires the subject to alter their motor behavior in order to contact the object (or potentially to change the goal to avoid the object or perform another action). In the present variant, contact time is controlled by having the object move towards the subject (interception task) rather than the subject move towards the object (reaching task), and by limiting the region of the workspace in which the subject can move his/her hand.

Figure 1B:
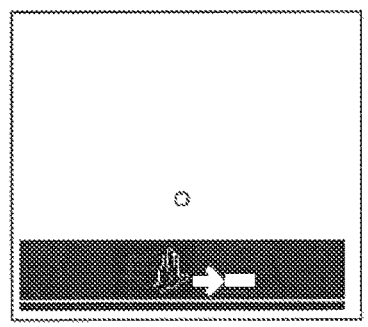
FIG. 1B is a schematic representation of different sensory events that may occur prior to the ball passing through the workspace in the fast feedback object intercept task.
Figure 1B:
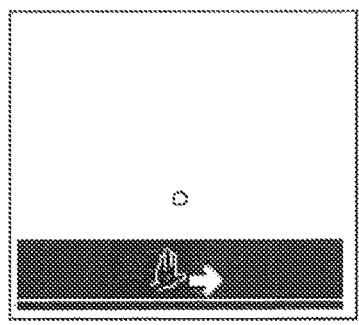
Figure 1B:
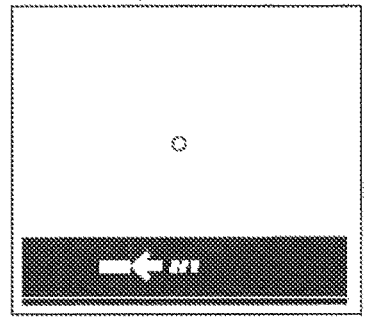
Figure 1B:
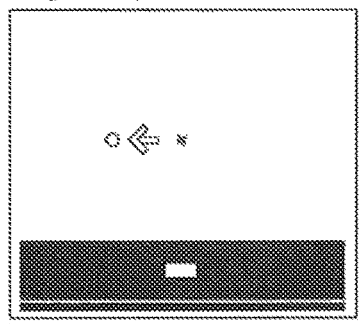
Figure 1C:
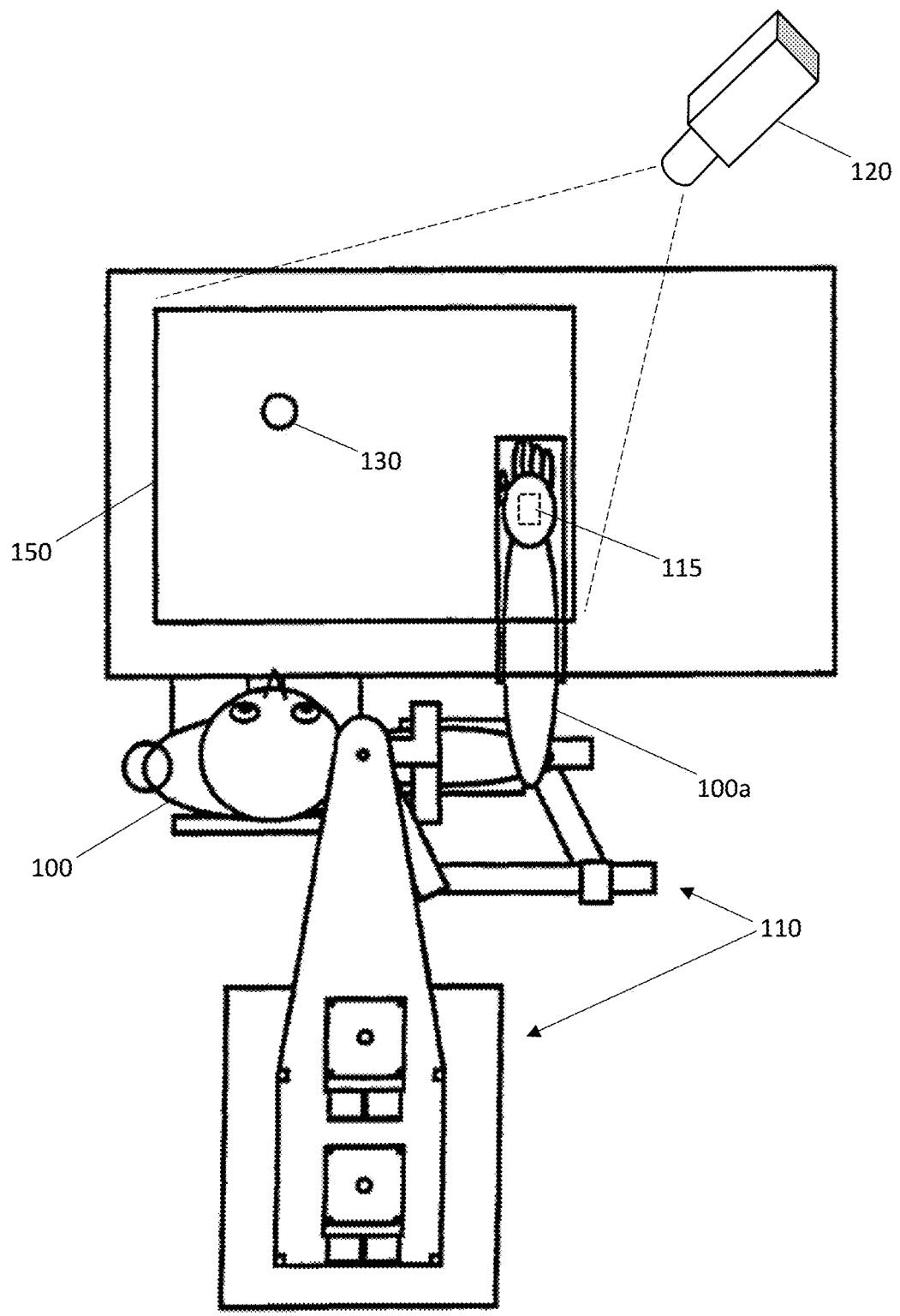
FIG. 1C is a diagram of a setup that may be used according to embodiments described herein, based on a mechanical linkage according to the prior art.

This unimanual target interception task requires a subject to hit (or avoid) a target moving towards the hand (FIG. 1A). As shown in FIG. 1C, the subject's limb 100a or at least hand is attached to a mechanical linkage 110 (e.g., KINARM, U.S. Pat. No. 6,155,993), or "robot". During the task, hand position represented by a virtual paddle is mechanically confined by the robot 110 into a small workspace displayed visually as a rectangular box 150 (e.g., 28 cm wide and 5 cm tall). The visual representation of this box is removed as the task starts, but the mechanical confinement applied by the robot remains. A single line also remains at the bottom edge of the box to help remind the subject they cannot move downwards (which would give them more time to hit the object). The task starts when the paddle is placed into a start box (a small hollow rectangle) located in the center of the workspace. The start box is then visually removed and a single white ball 130 appears at the top of the screen (e.g., 22.5 cm above center of workspace) and moves toward the virtual paddle at a constant speed (e.g., 25 cm/s). Prior to the start of the task, the subject is instructed that the objective of the task is to hit the target as it moves through the workspace. In this situation, given the limited size of the workspace and the constant speed of the ball, contact between the paddle and the ball is limited to a time window of about 200 ms. A simple variant of this task is to modify the height workspace (i.e., the dimension parallel to the ball's motion) to ensure a longer or an even shorter time window.

While the ball is moving towards the subject, one of six different conditions can occur (see FIGS. 1A and 1B):

1) The ball follows its initial trajectory so the subject must simply keep the paddle stationary at the initial position to hit the ball (Baseline);

2) Mechanical loads are applied to the limb, pushing the hand to the left or right and requiring the subject to quickly move back to the middle of the workspace to contact the target before it passes through the workspace. Vision of the paddle is provided throughout the correction (Mechanical with Vision);

3) Mechanical loads are again applied, but in this case, visual feedback of the paddle is removed at the moment the load is applied. This requires the subject to make a motor correction using only somatosensory feedback from the limb (Mechanical without Vision);

4) The position of the virtual paddle abruptly shifts (Cursor Jump) to the left or right requiring the subject to use visual feedback to move the paddle in the opposite direction back to the center of the workspace and hit the moving target;

5) The position of the ball abruptly shifts (Target Jump) to the left or right requiring the subject to use visual feedback to move the paddle in the same direction to hit the moving target; and 6) The color of the ball changes from white to red. Prior to the task the subject is instructed that if the target changes color they are not to intercept the target, but now must avoid the moving target (Task Switch: Don't Hit). This requires the subject to use visual information to move away from the center of the workspace in order to avoid hitting the object.

Thus, no shift trials are the baseline trials for holding posture. Physical shift trials mechanically perturb the arm to displace the hand horizontally with half the trials removing vision of the paddle. Target shift trials visually displace the ball horizontally while the ball continues to fall. Paddle shift trials visually displace the paddle horizontally. The physical or visual disturbance is applied when the ball is 10 cm above the center of the workspace so that the subject has 300 to 500 ms after this disturbance to contact the ball. Changes in the color of the ball in the Task Switch: Don't Hit trials occur when the ball is either 11.25 cm or 15 cm above the center of the workspace so that the subject has 350 to 550 ms, or 500 to 700 ms, respectively, to move the paddle away from the center of the workspace to avoid the ball. Subjects completed 24 trials for each condition randomly interleaved although a variant of this task could be to modify the proportion of trials so that some are more common and others are rare. Vertical speed of the ball is consistent unless it successfully contacts the paddle. Along with providing haptic feedback for this success, ball trajectory changes based on the conservation of momentum for the collision between the paddle and the ball.

Trials end when contact with the ball is made or when the ball reaches a thin (e.g., red) line at the bottom of the screen. The ball disappears and the start box reappears signifying the start of the next trial. Errors are generated for this task if the user: hits the ball before a condition initiates; is unable to hold the paddle in the start zone before a predetermined time (e.g., 15 s); or if the paddle goes below the thin red line at the bottom of the screen.

There are several critical benefits of this approach. First, control of the time between the sensory event and ball contact allows strategical assessment of the fastest goal-directed feedback pathways in the brain. Research highlights that goal-related sensory feedback processing can generate muscle responses in as little as 60 ms with motor corrections observable in less than 200 ms (Scott, 2016). If a subject can move to reach a stationary or moving target, the time of object contact cannot be controlled, particularly for subjects with poor motor coordination that must make many corrective movements when attaining a goal. Critically, if the subject controls the time of contact they can delay contact, diminishing the urgency for the corrective response and diminishing the use of the fastest feedback pathways (Crevecoeur et al., 2013).

Second, different types of sensory feedback processing take different amounts of time. Goal-directed motor corrections to mechanical disturbances begin at 60 ms, visual-based motor corrections begin at 100 ms, whereas implementing cognitive rules like switching to avoiding an object based on a visual cue takes ~200 ms. By controlling contact time, the sensory events can be adjusted individually (color change would occur 100 ms earlier than if a mechanical disturbance would occur). Again, controlling the time of contact is crucial for this level of control of subject behavior.

Third, initiating the task with the object directly moving to the position of the virtual paddle minimizes differences in baseline behavior prior to the sensory event. There is considerable trial-to-trial variability in subject performance when reaching to a spatial goal, and even more variability in performance across subjects, as such movements are relatively straight but commonly have small systematic curvatures (Morasso, 1982; Sergio and Scott, 1999). In patient groups, such as subjects with stroke, this variability increases enormously as their movements become slower and jerky with many corrective movements. This large heterogeneity in baseline movement makes it difficult to identify movement related to the motor correction generated by the sensory event from that related to the baseline movement to the goal. Positioning the virtual paddle at the beginning of the trial directly in the path of the ball means that the subject must simply maintain the hand at a fixed posture and wait for ball contact. This greatly reduces inter-subject variability so that any movement from this postural position reflects a motor correction to the sensory event.

A final benefit of this task design is time per trial particularly for a subject with difficulty making quick movements. The time for each trial is dependent on the speed of the moving ball instead of the maximal speed the subject can move to an object. This allows many trials to be collected in a shorter amount of time.

This task is distinct from previous behavioural tasks that also used moving objects and subjects had to use paddles to hit objects in the environment, such as the tasks described in Tyryshkin et al. (2014) and U.S. Pat. No. 8,740,794. That prior task used one or more moving objects in the workspace and the subject was free to hit the objects with paddles virtually attached to either hand. This prior task cannot address the question of motor corrections as the subject has a second or more to hit each object, well beyond the time window for assessing fastest feedback processing by the brain. The hands are free to move throughout a large workspace so there are substantial differences in the baseline behavior making it impossible to quantify a motor response to a target from their ongoing baseline behavior.

The task described herein is distinct from previous studies that have applied mechanical disturbances when a subject is maintaining their hand at a spatial target (Bourke et al., 2015). Such tasks do not intrinsically control time to attain the goal (in this case return to the target) and must use post-trial feedback (such as a color cue to try to train the subject the appropriate time to contact or that they are too slow and must go faster). Target jumps and cursor jumps are difficult to separate when the hand and target are in the same spatial location, adding a cognitive component that delays feedback processing and does not allow one to specifically test the fastest visual feedback processes.

Participants

Subjects with stroke were recruited from the stroke rehabilitation wards at Providence Care Hospital in Kingston, Ontario, Canada. All subjects had a single stroke that resulted in a lesion on one side of the brain and subjects were categorized into right affected (RA) or left affected (LA) based on the most affected side of the body. A total of 10 subjects with stroke were recruited (5 RA, and 5 LA). Twenty-one healthy control subjects (people with no neurological injuries or disorders) were recruited from the community. Participants were excluded if they could not understand the task instructions.

Data Analysis

Data analyses were performed using MATLAB (The Mathworks, Inc., Massachusetts, USA).

Example parameters used for this task are quantified based on two time points: the time of perturbation onset and the end of the trial. The time of perturbation onset is the time when the ball reaches a selected distance from the center of the workspace. The end of the trial is the time when the ball contacts the paddle or when it reaches the bottom of the workspace (i.e., a thin red line at the bottom of the screen.

Endpoint Distance. This is the horizontal distance (X axis) from the center of the ball to the center of the paddle at the end of the trial.

Hit Speed. The horizontal speed of the paddle at the end of the trial.

Maximum Acceleration. The maximum horizontal acceleration of the hand from the time of perturbation onset to the end of the trial.

Maximum Speed. The fastest horizontal movement of the paddle from the time of perturbation onset to the end of the trial.

Maximum Distance. The furthest horizontal distance that the paddle was displaced from the time of perturbation onset to the end of the trial.

Mean Speed. The total horizontal distance traveled by the paddle divided by the time from perturbation onset to the end of the trial.

Posture Speed. The total horizontal distance traveled by the paddle divided by the time when the ball appeared and started moving to the time of perturbation onset.

Mid Speed. The horizontal speed of the paddle at the point when the ball was at the center of the workspace.

Mid Distance. The horizontal distance of the paddle at the point when the ball was at the center of the workspace.

Number of Misses. The number of trials in which the subject was unable to successfully make contact with the ball.

Reaction Time. Reaction time is a measure of movement onset related to a disturbance.

Movement onset is defined as the earlier time point between 1) the first point when the velocity reaches 10% of the maximum velocity or 2) when the acceleration reaches 25% of the maximum acceleration.

Results

Exemplar Participants

Figure 2A:
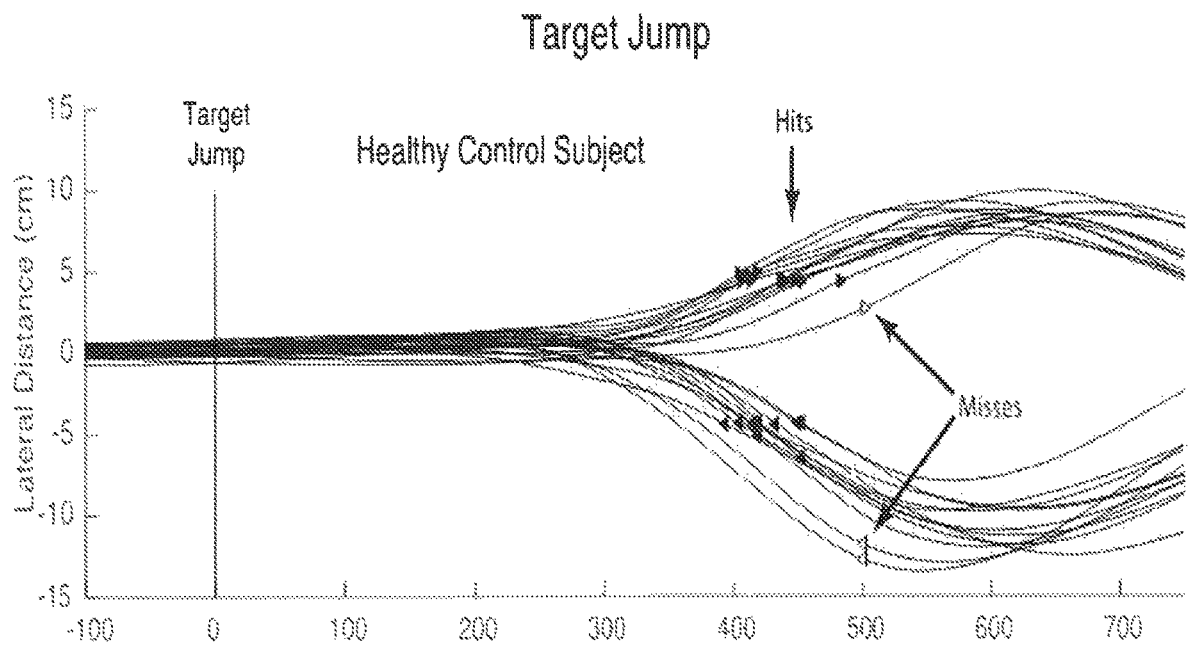
FIG. 2A is a plot of paddle position in the X direction (lateral to the body) for a healthy control subject aligned to the onset of a target jump, wherein filled triangles denote successful contact with the ball and open triangles denote subject did not contact the ball.
Figure 2B:
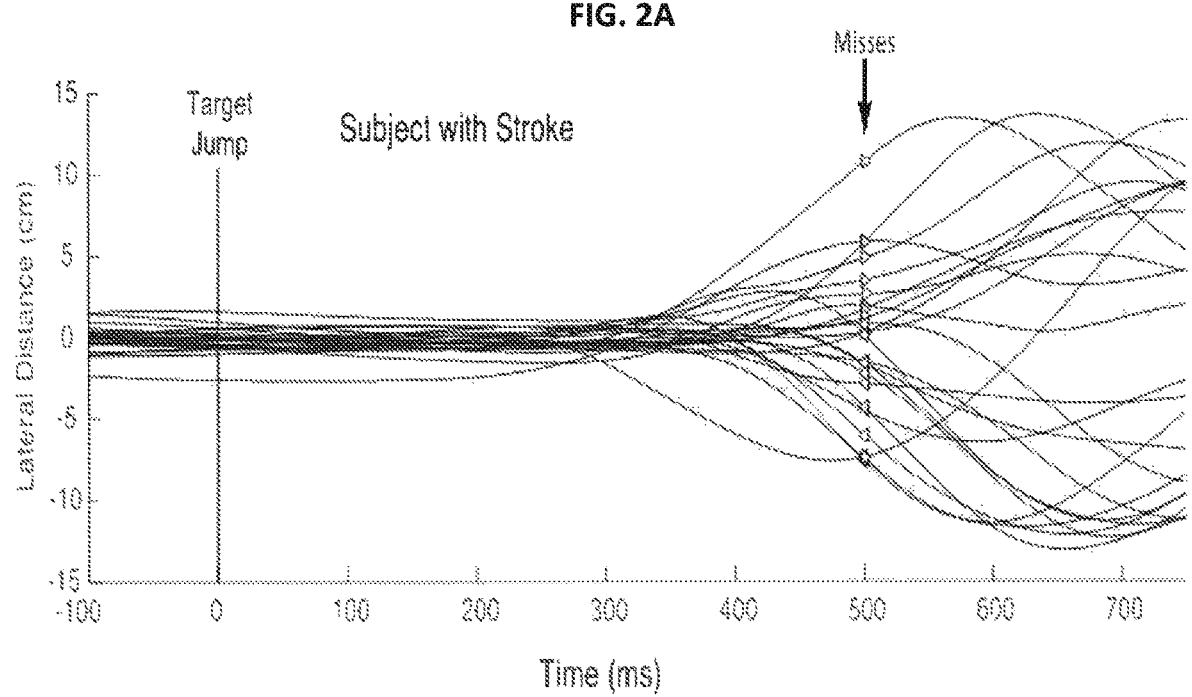
FIG. 2B is a plot of paddle position in the X direction (lateral to the body) for a subject with stroke aligned to the onset of a target jump, wherein open triangles denote subject did not contact the ball on the trial.

Lateral (X) paddle position (zero is start position) is displayed in FIG. 2A for a healthy control subject for the Target Jump trials. Trials are aligned relative to target jump. Filled triangles denote trials in which the subject generated a corrective response and hit the target, whereas empty triangles denote trials in which the subject did not hit the object. FIG. 2B displays performance by a subject with stroke and highlights how the subject was not able to respond to hit any of the objects as they passed through the workspace as motor corrections. The healthy control subject initiated the motor correction at ~300 ms, whereas the motor corrections were slower with many trials ~400 ms or more for the subject with stroke.

Figure 3A:
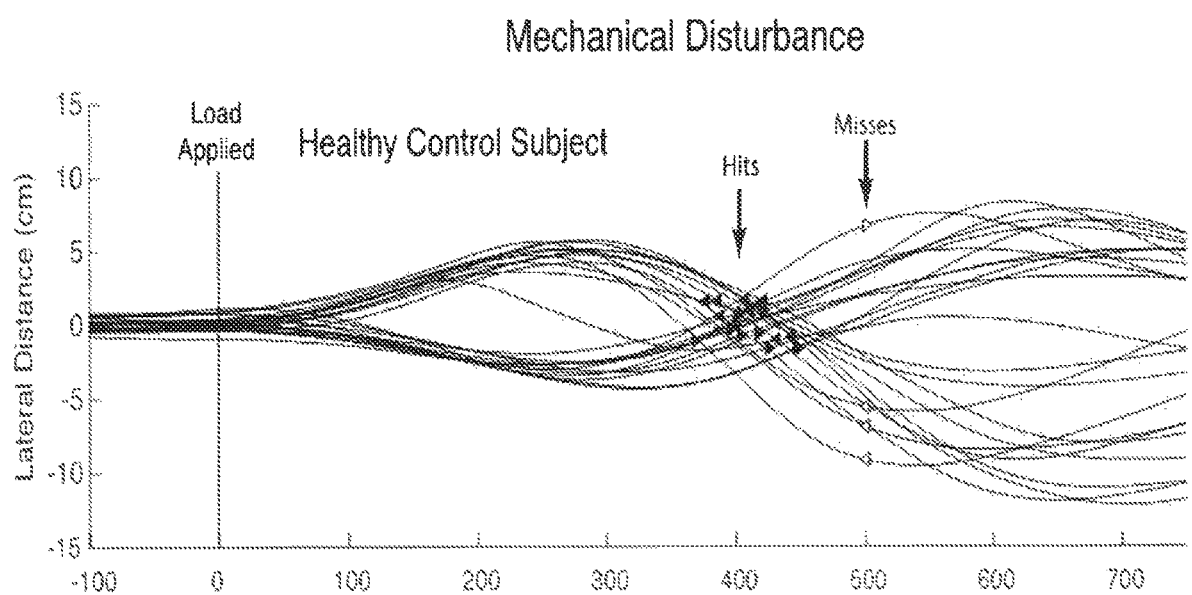
FIG. 3A is a plot of paddle position in the X direction (lateral to the body) for a healthy control subject aligned to the onset when a load was applied to the arm, wherein filled triangles denote successful contact with the ball and open triangles denote subject did not contact the ball.
Figure 3B:
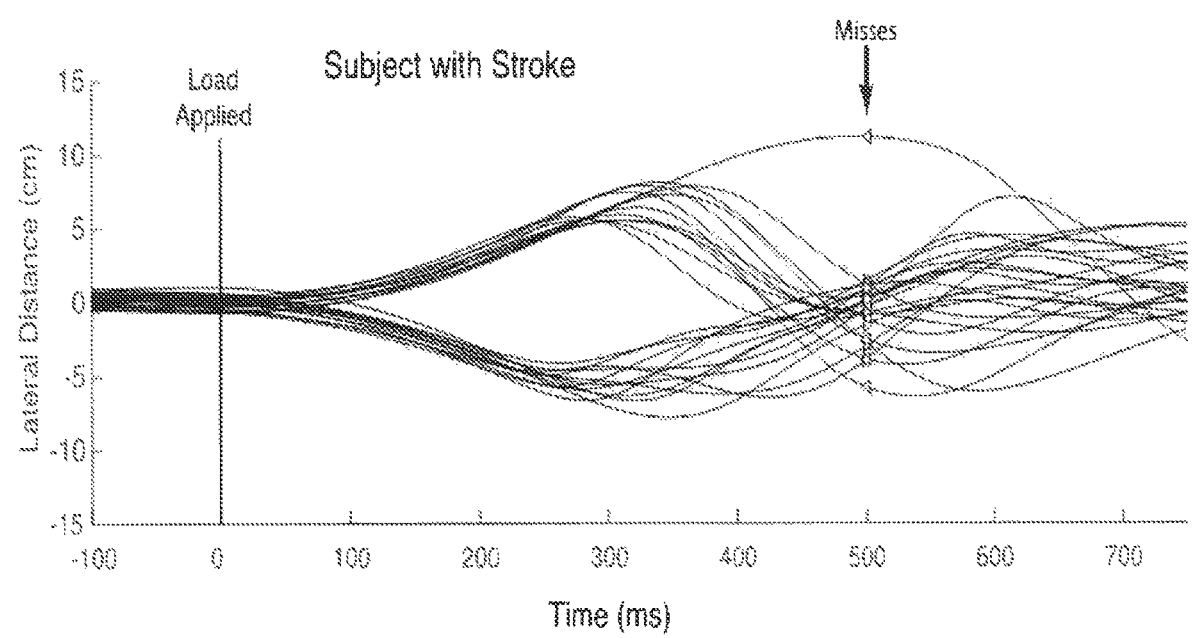
FIG. 3B is a plot of paddle position in the X direction (lateral to the body) for a subject with stroke aligned to the onset when a load was applied to the arm, wherein open triangles denote subject did not contact the ball on the trial.
Figures 4A, 4B, 4C, 4D, 4E:
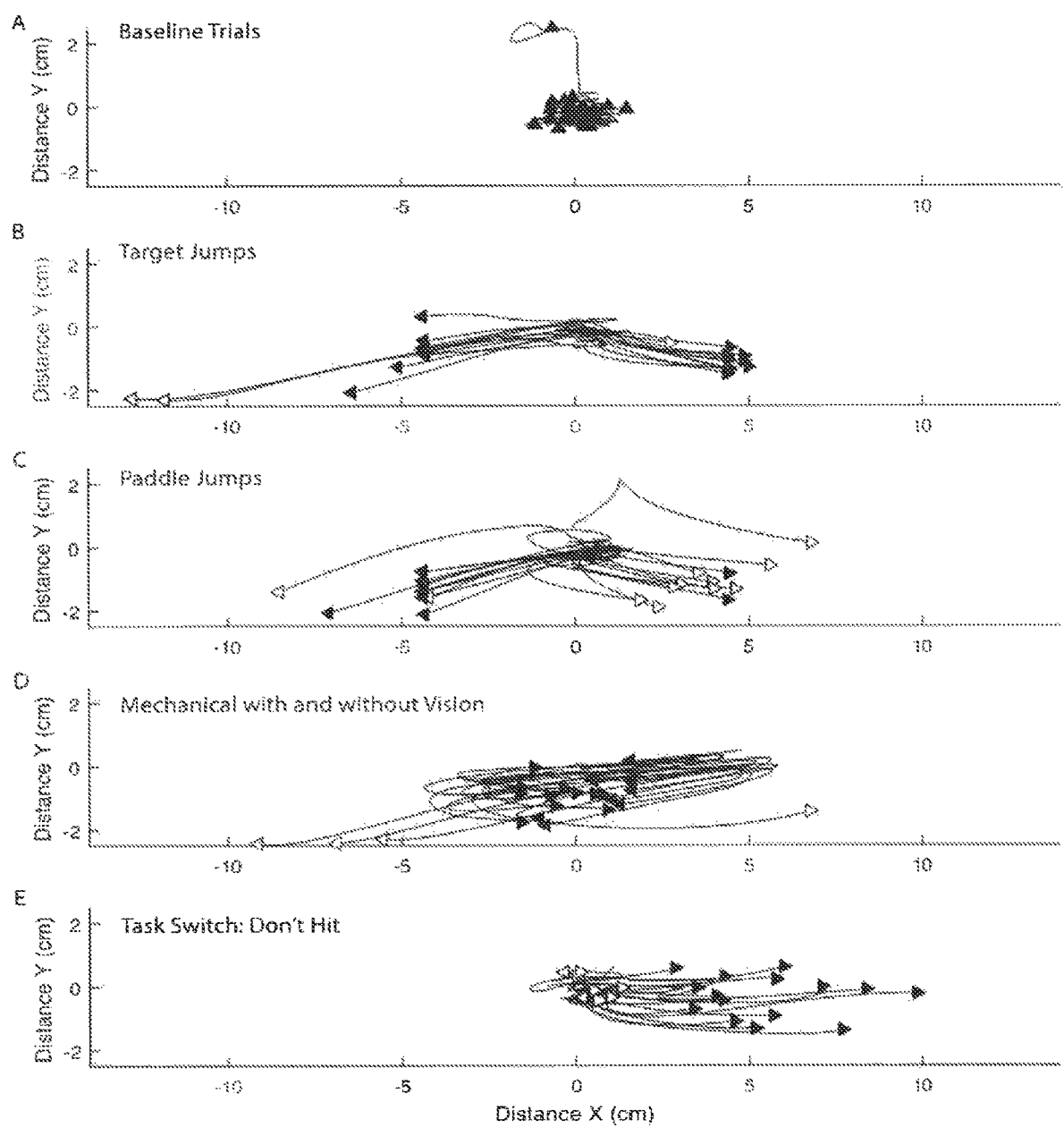
FIG. 4A is a plot of hand position in the workspace during Baseline trials for a healthy control subject.
FIG. 4B is a plot of hand position in the workspace during Target Jump trials for a healthy control subject.
FIG. 4C is a plot of hand position in the workspace during Paddle Jumps for a healthy control subject.
FIG. 4D is a plot of hand position in the workspace during Mechanical Disturbances for a healthy control subject.
FIG. 4E is a plot of hand position in the workspace during Don't Hit trials for a healthy control subject.
Figures 5A, 5B, 5C, 5D, 5E:
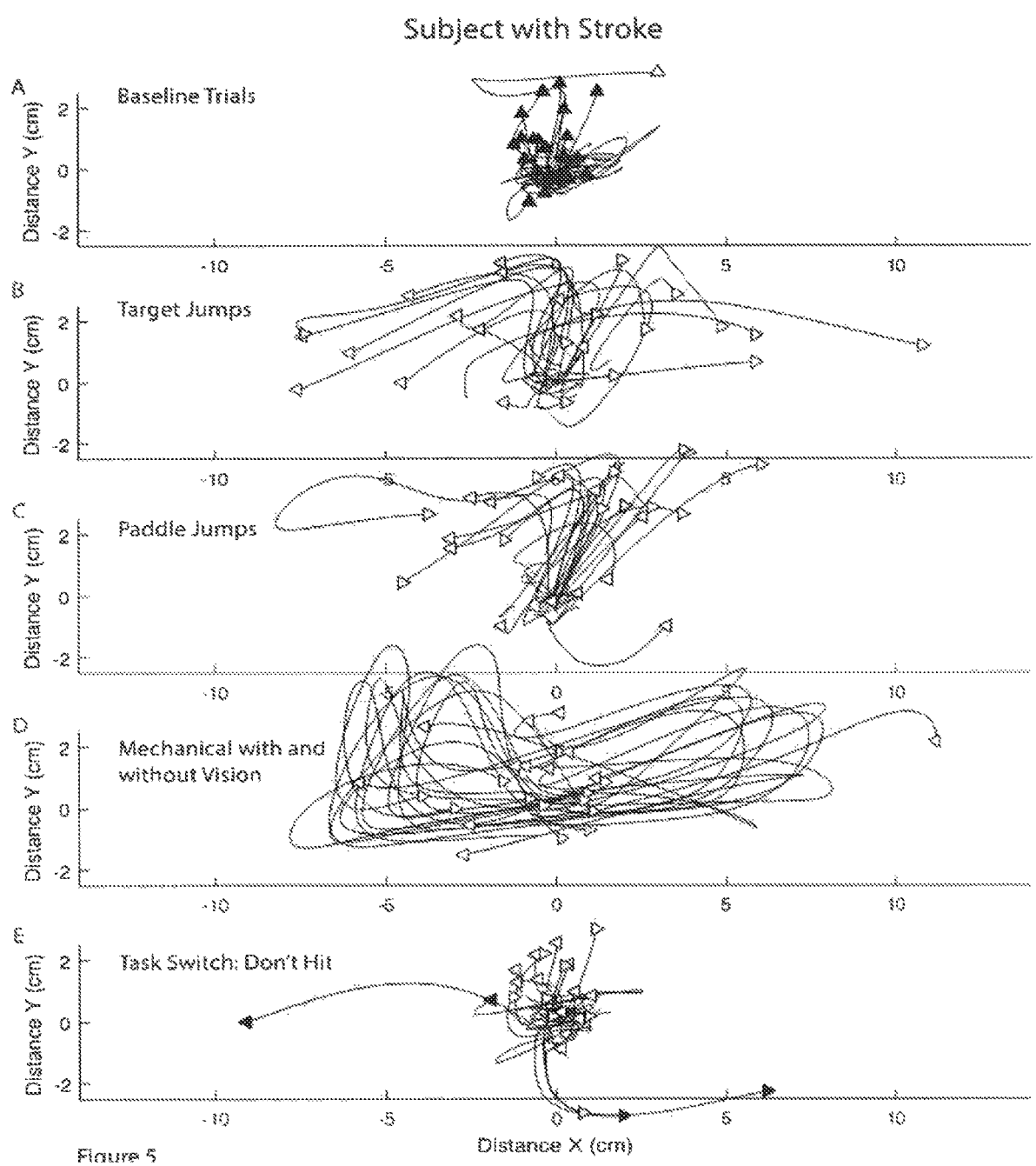
FIG. 5A is a plot of hand position in the workspace during Baseline trials for a subject with stroke.
FIG. 5B is a plot of hand position in the workspace during Target Jump trials for a subject with stroke.
FIG. 5C is a plot of hand position in the workspace during Paddle Jumps for a subject with stroke.
FIG. 5D is a plot of hand position in the workspace during Mechanical Disturbances for a subject with stroke.
FIG. 5E is a plot of hand position in the workspace during Task Switch: Don't Hit trials for a subject with stroke.
Figures 6A, 6B, 6C, 6D:
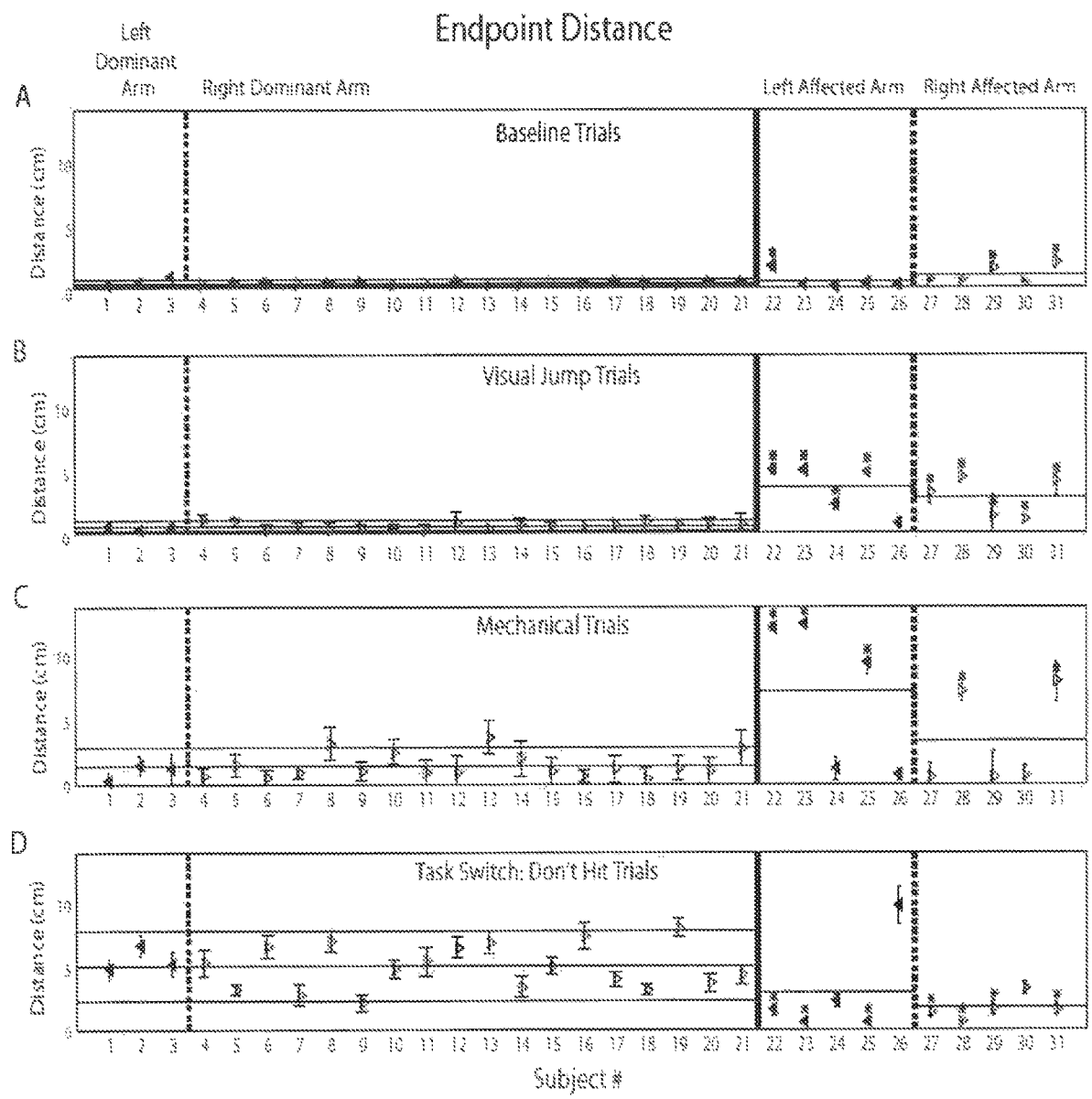
FIG. 6A is a plot of Lateral Distance between ball and Paddle during Baseline Trials for healthy control subjects and subjects with stroke.
FIG. 6B is a plot of Lateral Distance between ball and Paddle during Visual Shift Trials (Target Jump and Paddle Jumps combined) for healthy control subjects and subjects with stroke.
FIG. 6C is a plot of Lateral Distance between ball and Paddle during Mechanical Disturbances for healthy control subjects and subjects with stroke.
FIG. 6D is a plot of Lateral Distance between ball and Paddle during Task Switch: Don't Hit trials for healthy control subjects and subjects with stroke.

Lateral (X) Paddle Position (zero is start position) is displayed in FIG. 3A for a healthy control subject when mechanical disturbances are applied. The applied load moved the hand either to the right (positive values) or left (negative values), and the subject generated motor corrections to return the hand to the central position and hit the ball (filled triangles) on most trials and missed the ball on only three trials (open triangles). Performance by a subject with stroke is displayed in FIG. 3B and highlights that the subject never contacted the ball following the mechanical disturbances. The kinematics highlight how motor corrections were delayed for the stroke subject as compared to the healthy control subject and hand deviations from the central position were larger.

Hand paths in the workspace are displayed for a healthy control subject (FIGS. 4A-4E) and for a subject with stroke (FIGS. 5A-5E). In each figure panels A, B, C, D and E show the Baseline, Target Jump, Paddle Jump, Mechanical Disturbance with and without Vision, and Task Switch: Don't Hit trials, respectively. Each panel displays the trajectory of the paddle for each trial from the time of the sensory event to the time of contact or end of trial (ball leaves workspace). Triangles point in the direction required to successfully contact the ball. Filled triangles represent successful trials: hit the ball or in the case of Don't Hit trials, miss the ball. Open triangles represent unsuccessful trails. The control subject was successful on most trials and exhibited fairly consistent performance across trials, whereas the subject with stroke failed many more trials and was highly inconsistent across trials.

All Participants

The endpoint distance (absolute Lateral Distance X from center of paddle to the center of the paddle at ball contact or end of trial) for all subjects is shown in FIGS. 6A-6D. The panels show the Baseline trials (FIG. 6A), Target and Cursor Jumps (FIG. 6B), Mechanical with and without Vision (FIG. 6C), and Don't Hit trials (FIG. 6D. The data show: 1) 3 control subjects with a dominant left arm, 2) 18 control subjects with a dominant right arm, 3) 5 subjects whose left arm was more affected by stroke, 4) 5 subjects whose right arm was more affected by stroke. Triangle direction and fill indicates the dominant or more affected arm. Healthy control performance is for the dominant arm, whereas performance for the most affected arm is displayed for the subjects with stroke.

Control subjects show consistent performance for each type of trial across baseline, visual, and mechanical trials with mean values close to zero and low variability across the population. Stroke subjects for these trial types show higher mean values as well as higher variability compared to the control subjects. The Task Shift:Don't Hit trials for the control subjects showed a high mean value indicating they successfully moved away from the ball as it passed through the workspace. The stroke subjects showed a lower mean value indicative of poorer performance in trying to avoid the ball. The shaded region denotes the $5^{th}$ and $95^{th}$ percentile paddle positions for healthy control subjects. Asterisks identify performance by subjects with stroke that was greater than $95^{th}$ percentile of healthy control performance for Visual and Mechanical disturbances and below 5S percentile of healthy controls performance for Task Switch: Don't Hit.

Some stroke subjects displayed distinct patterns of impairment. Subjects 23 and 28 were impaired in all types of feedback processing. In contrast, subjects 27 and 29 displayed no impairments for mechanical disturbances, but showed impairments associated with visual or cognitive feedback processing. Finally, subject 24 only exhibited impairments associated with visual jump trials.

All cited publications are incorporated herein by reference in their entirety.

EQUIVALENTS

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

REFERENCES

Bourke, T. C., Coderre, A. M., Bagg, S. D., Dukelow, S. P., Norman, K. E. and Scott, S. H. Impaired corrective responses to postural perturbations of the arm in individuals with subacute stroke. *Journal of Neuroengineering and Rehabilitation* 12:7 (2015).

Brenner, E. & Smeets, J. B. J. Fast corrections of movements with a computer mouse. *Spatial Vision* 16, 365-376 (2003).

Cluff, T., Scott, S. H. Apparent and actual trajectory control depend on the behavioural context in upper limb motor tasks. *Journal of Neuroscience* 35(36):12465-12476 (2015a).

Cluff, T., Crevecoeur, F. and Scott, S. H. A perspective on multisensory integration and rapid perturbation responses. *Vision Research* 110:215-222 (2015b).

Crevecouer, F., Kurtzer, I., Bourke, T. and Scott, S. H. Feedback responses rapidly scale with the urgency to correct external perturbations. *Journal of Neurophysiology* 110:1323-1332 (2013).

Goodale, M. A., Pelisson, D. & Prablanc, C. Large adjustments in visually guided reaching do not depend on vision of the hand or perception of target displacement. *Nature* 320, 748-750 (1986).

Kandel, E. R., Schwartz, J. H., Jessell, T. M., Siegelbaum, S. A. and Hudspeth, A. J. *Principles of Neural Science*, $5^{th}$ Ed., McGraw Hill. New York (2013).

Morasso, P. Spatial control of arm movements. *Experimental Brain Research* 42:223-227 (1981).

Scott, S. H. A functional taxonomy of bottom-up sensory feedback processing for motor actions. Trends in *Neuroscience* 39:512-526 (2016).

Sergio, L. H. and Scott, S. H. Hand and joint paths during reaching movements with and without vision. *Experimental Brain Research* 122:157-164 (1998).

Tyryshkin, K., Coderre, A., Glasgow, J., Herter, T. M., Dukelow, S. P., Bagg, S. D. and Scott, S. H. A robotic hitting task to quantify sensorimotor impairments in subjects with stroke. *Journal of Neuroengineering and Rehabilitation* 11:47 (2014).

VanDeusen, J. and Brunt, D *Assessment in Occupational Therapy and Physical Therapy*, Philadelphia: W.B. Saunders Co. (1997).

The invention claimed is:

1. A method for assessing sensorimotor performance of a subject, comprising:
   i) using a mechanical linkage attached to at least a portion of one limb of the subject or grasped by the subject to restrict movement of the at least a portion of the limb of the subject to movement within a workspace;
   ii) using a display device to present a single object to the subject, wherein the object moves towards a position of the at least a portion of the limb in the workspace;
   iii) using one or more sensors to obtain position data and/or motion data and/or kinetic data of the limb or one or more portions thereof with respect to the object as the subject interacts with the object;
   iv) repeating ii and iii for a plurality of trials;
   wherein, for each trial, the subject performs a task in response to the presented object;
   wherein, for a portion of the plurality of trials, a perturbation is applied that requires the subject to make at least one rapid motor correction to complete the task;
   wherein the perturbation is applied after the object is presented and is at least one of a perturbation applied to the at least a portion of the limb of the subject by the mechanical linkage, a change related to a position of a representation of the at least one portion of the subject's limb on the display device, and a change related to the presented object by the display device;
   v) using computer software to construct and analyze a data set from the obtained position data and/or motion data and/or kinetic data for the plurality of trials and output a result, wherein analyzing comprises determining a parameter of the position and/or motion and/or kinetics of the subject's limb or portion thereof during a time period of less than one second from when the perturbation is applied; and
   vi) wherein the result is information about the subject's ability to generate the at least one rapid motor correction within the time period of less than one second after the perturbation is applied.

2. The method of claim 1, wherein each perturbation is the same or different and is selected from perturbing the movement of the object, perturbing motion of the limb or the at least one portion thereof, and changing a feature of the object such that the subject must respond to the change by either interacting with the object or avoid interacting with the object.

3. The method of claim 1, wherein the time period is adjusted according to a selected perturbation.

4. The method of claim 1, wherein at least one perturbation includes changing a feature of the object such that the subject must respond to the change by either interacting with the object or avoid interacting with the object requires that the subject's motor response is different than the motor response initially instructed.

5. The method of claim 1, comprising obtaining data relating to one or more autonomic functions of the subject.

6. The method of claim 1, comprising presenting the object to the subject using virtual reality or augmented reality in two or three dimensions.

7. The method of claim 1, comprising using a motion tracking system to obtain the position data and/or motion data and/or kinetic data of the limb or the at least one portion of the limb.

8. The method of claim 1, comprising determining kinetic trajectory data of the limb or the at least one portion of the limb with respect to the presented object.

9. The method of claim 1, comprising determining speed and/or velocity of the limb or the at least one portion of the limb with respect to the presented object.

10. The method of claim 1, comprising obtaining gaze position data as the subject interacts with the presented object.

11. The method of claim 1, wherein obtaining the position data and/or motion data and/or kinetic data of the limb or the at least one portion of the limb comprises using the mechanical linkage attached to the limb, or the mechanical linkage grasped by the subject, or the one or more sensors attached to the limb, and related hardware for detecting output signals from the one or more sensors.

12. The method of claim 1, wherein assessing comprises diagnosing or detecting brain injury and/or a neurological disorder of the subject;
wherein the result provides information about brain injury and/or a neurological disorder motor activity in the subject.

13. The method of claim 1, wherein assessing comprises determining skill level of the subject performing an activity;
wherein the result provides information about skill level in the subject.

14. The method of claim 13, wherein the activity is a sport.

15. Apparatus for assessing sensorimotor performance of a subject, comprising:
a mechanical linkage configured to be attached to a limb of the subject or grasped by the subject, wherein the mechanical linkage is adapted to restrict movement of the limb or at least one portion of the limb to movement within a workspace;
a display device configured to present a single object to the subject, wherein the object moves towards a position of the at least one portion of the limb within the workspace;
one or more sensors configured to attach to the at least one portion of the limb and/or the mechanical linkage that provide position data and/or motion data and/or kinetic data of the at least one portion of the limb as the subject interacts with the presented object;
wherein the apparatus is configured to use computer software to construct and analyze a data set including the one or more of position data, motion data, and kinetic data of the limb or the at least one portion of the limb obtained from the one or more sensors as the subject performs a task in response to the presented object during a plurality of trials, and output a result;
wherein the apparatus is adapted to apply a perturbation that requires the subject to make at least one rapid motor correction to complete the task for a portion of the plurality of trials;
wherein the perturbation is applied after the object is presented and is at least one of a perturbation applied to the at least a portion of the limb of the subject by the mechanical linkage, a change related to a position of a representation of the at least one portion of the subject's limb on the display device, and a change related to the presented object by the display device;
wherein the analysis comprises determining using the computer software to determine a parameter of the position and/or motion and/or kinetics of the subject's limb or portion thereof during a time period of less than one second from when the perturbation is applied;
wherein the result is information about the subject's ability to generate the at least one rapid motor correction within the time period of less than one second after the perturbation is applied.

16. The apparatus of claim 15, wherein the display device is adapted to display a change in at least one feature of the presented object.

17. The apparatus of claim 15, wherein the display device is adapted to present the object to the subject using virtual reality or augmented reality in two or three dimensions.

* * * * *

UNITED STATES PATENT AND TRADEMARK OFFICE
CERTIFICATE OF CORRECTION

| | |
|---|---|
| PATENT NO. | : 11,547,325 B2 |
| APPLICATION NO. | : 16/408656 |
| DATED | : January 10, 2023 |
| INVENTOR(S) | : Stephen H. Scott and Kayne Park |

It is certified that error appears in the above-identified patent and that said Letters Patent is hereby corrected as shown below:

In the Claims

Claim 15, Column 16, Line 30, delete "determining"

Signed and Sealed this
Fourth Day of April, 2023

Katherine Kelly Vidal
*Director of the United States Patent and Trademark Office*